United States Patent
Yoshikawa et al.

(10) Patent No.: US 10,501,088 B2
(45) Date of Patent: Dec. 10, 2019

(54) ROAD SURFACE STATE DETERMINATION APPARATUS, IMAGING APPARATUS, IMAGING SYSTEM, AND ROAD SURFACE STATE DETERMINATION METHOD

(71) Applicant: KYOCERA Corporation, Kyoto-shi, Kyoto (JP)

(72) Inventors: Atsushi Yoshikawa, Sagamihara (JP); Takatoshi Nakata, Yokohama (JP); Tomohiro Mitsugi, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 15/769,573

(22) PCT Filed: Aug. 29, 2016

(86) PCT No.: PCT/JP2016/003929
§ 371 (c)(1),
(2) Date: Apr. 19, 2018

(87) PCT Pub. No.: WO2017/068743
PCT Pub. Date: Apr. 27, 2017

(65) Prior Publication Data
US 2018/0304898 A1    Oct. 25, 2018

(30) Foreign Application Priority Data

Oct. 22, 2015  (JP) .................. 2015-208243

(51) Int. Cl.
*B60W 40/06* (2012.01)
*G01N 21/17* (2006.01)
*G06K 9/00* (2006.01)

(52) U.S. Cl.
CPC ............ *B60W 40/06* (2013.01); *G01N 21/17* (2013.01); *G06K 9/00791* (2013.01); *B60W 2420/42* (2013.01); *G01N 2021/1765* (2013.01)

(58) Field of Classification Search
CPC .. B60W 40/06; B60W 2420/42; G01N 21/17; G01N 2021/1765; G06K 9/00791
See application file for complete search history.

(56) References Cited

U.S. PATENT DOCUMENTS

| | | | |
|---|---|---|---|
| 5,963,148 A  * | 10/1999 | Sekine ................ | G01C 21/26 340/905 |
| 2003/0001509 A1 | 1/2003 | Leleve | |
| 2015/0116462 A1* | 4/2015 | Makabe ................ | B60R 1/002 348/47 |

FOREIGN PATENT DOCUMENTS

| | | | |
|---|---|---|---|
| JP | H2-161337 A | | 6/1990 |
| JP | H08-247940 A | | 9/1996 |
| JP | H10-221043 A | | 8/1998 |
| JP | H 0221043 A | * | 8/1998 |

(Continued)

OTHER PUBLICATIONS

English Translation for reference JPH10221043A (Year: 1998).*

*Primary Examiner* — Rachid Bendidi
(74) *Attorney, Agent, or Firm* — Procopio Cory Hargreaves and Savitch LLP

(57) ABSTRACT

A road surface state determination apparatus of the present disclosure includes an acquisition interface configured to acquire an image representing a road surface imaged by a camera, and a controller configured to determine whether the road surface is wet or dry on the basis of a spatial change in luminance of pixels in a continuous region included in the image.

9 Claims, 11 Drawing Sheets

(56) References Cited

FOREIGN PATENT DOCUMENTS

| | | |
|---|---|---|
| JP | 2002-286862 A | 10/2002 |
| JP | 3552504 B2 | 5/2004 |
| JP | 2004-279279 A | 10/2004 |
| JP | 2008-027046 A | 2/2008 |
| JP | 2009-222529 A | 10/2009 |
| JP | 2011-174794 A | 9/2011 |
| JP | 2012-194872 A | 10/2012 |

* cited by examiner

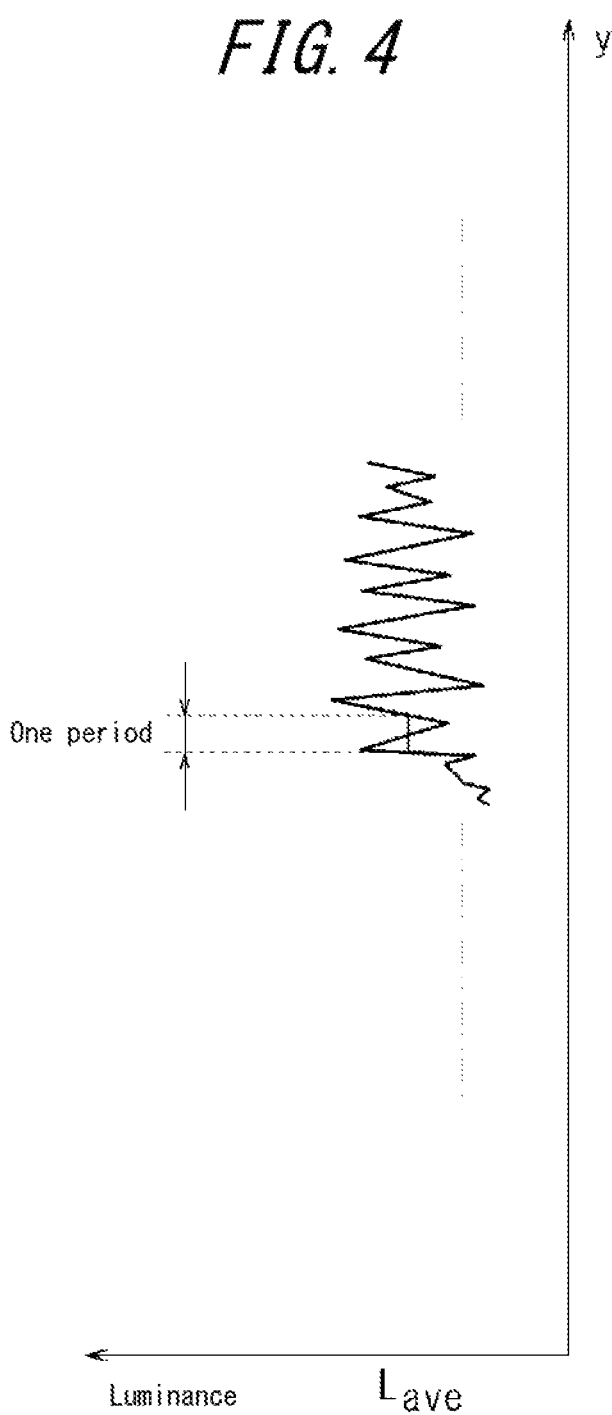

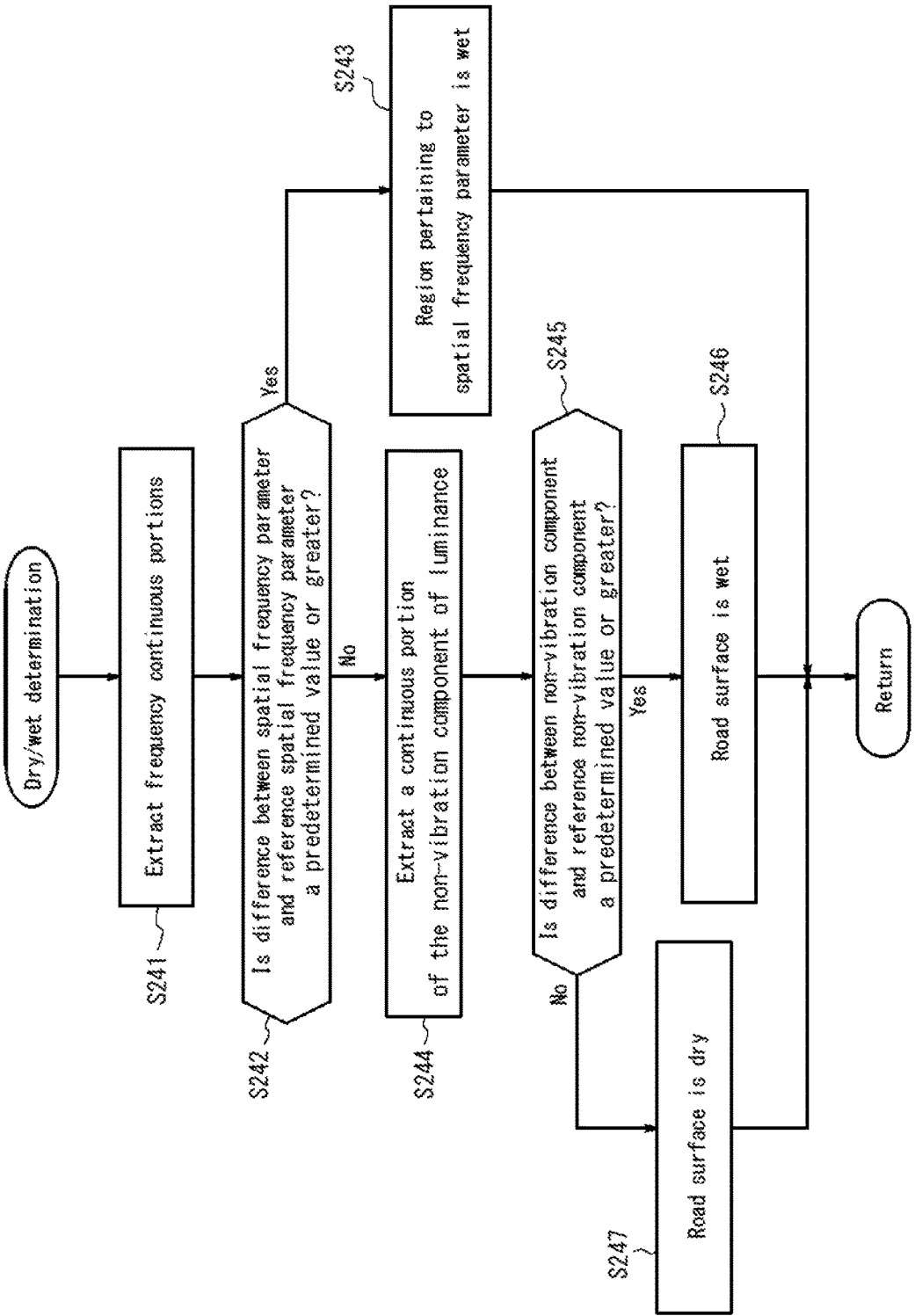

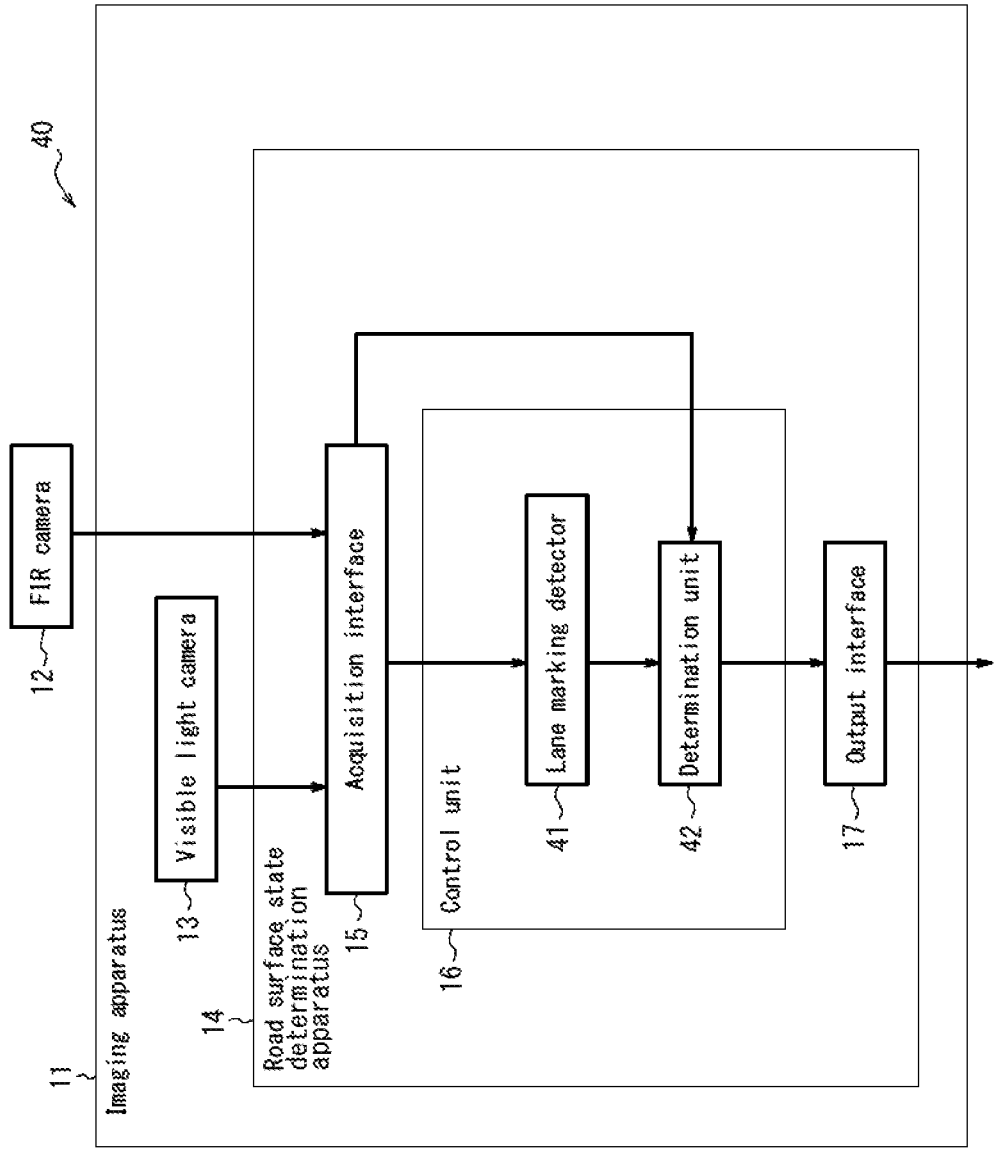

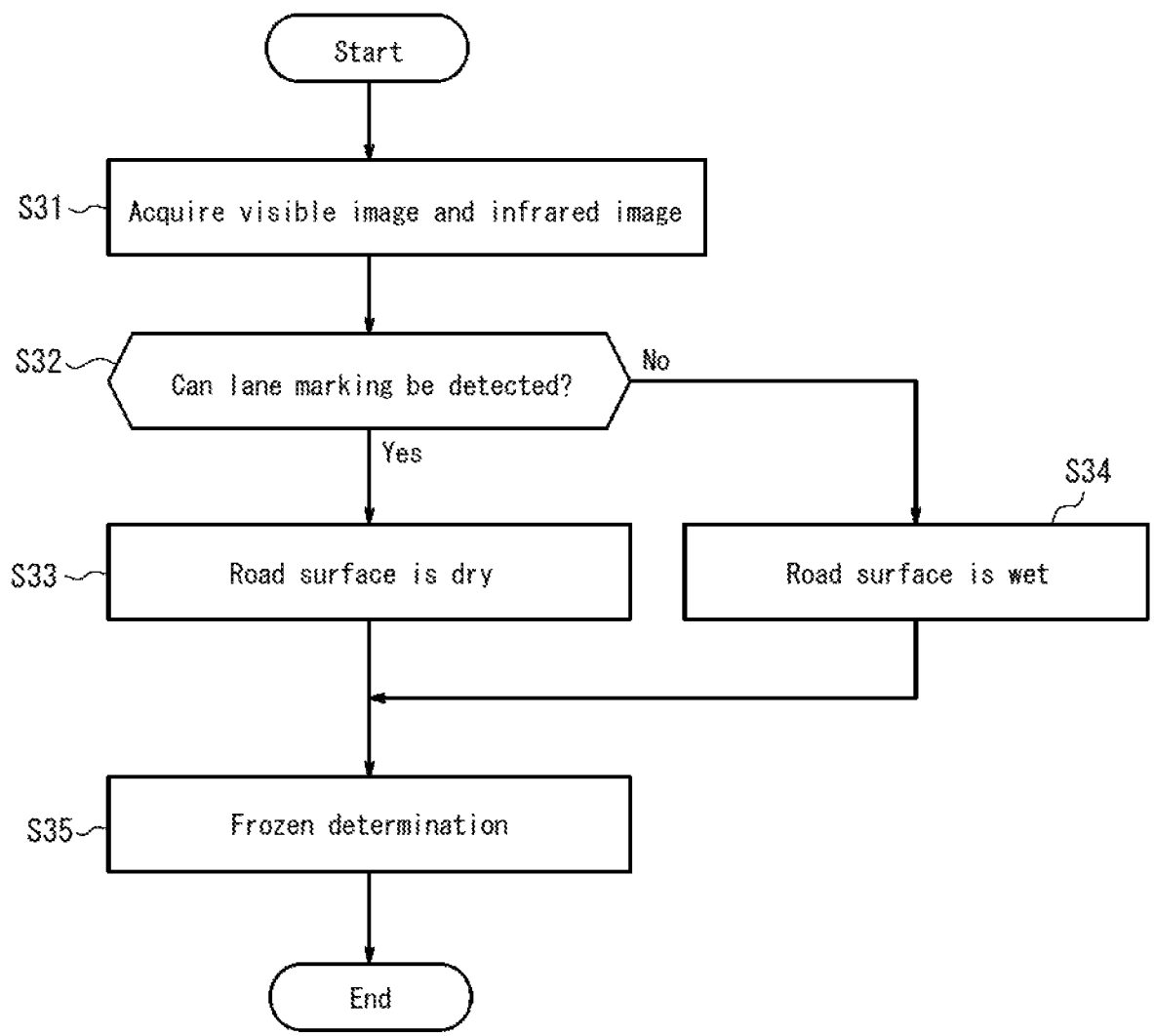

ROAD SURFACE STATE DETERMINATION APPARATUS, IMAGING APPARATUS, IMAGING SYSTEM, AND ROAD SURFACE STATE DETERMINATION METHOD

CROSS-REFERENCE TO RELATED APPLICATION

The present application claims priority to and the benefit of Japanese Patent Application No. 2015-208243 filed Oct. 22, 2015, the entire contents of which are incorporated herein by reference.

TECHNICAL FIELD

The present disclosure relates to a road surface state determination apparatus, an imaging apparatus, an imaging system, and a road surface state determination method.

BACKGROUND

Methods used in vehicles, such as automobiles, have been developed for acquiring information on people, other vehicles, obstacles, the road surface, and the like in the direction in which a vehicle is traveling. This information is then used for driving assistance, such as warning the driver to avoid a vehicle collision, braking automatically, or controlling the accelerator for cruise control.

Vehicle driving is affected by the state of the road surface on which the vehicle travels. For example, to drive the vehicle in the desired direction at the desired speed, the driver brakes and steers differently depending on the state of the road surface, such as whether the road surface is frozen, wet, or dry. Outputting information based on the state of the road surface to get the driver's attention and transmitting such information to an apparatus for supporting vehicle control are also useful for supporting safe driving.

SUMMARY

The road surface state determination apparatus of the present disclosure comprises an acquisition interface and a controller. The acquisition interface is configured to acquire an image representing a road surface imaged by a camera. The controller is configured to determine whether the road surface is wet or dry on the basis of a spatial change in luminance of pixels in a continuous region included in the image.

An imaging apparatus of the present disclosure comprises a camera and a road surface state determination apparatus. The road surface state determination apparatus comprises an acquisition interface and a controller. The acquisition interface is configured to acquire an image representing a road surface imaged by the camera. The controller is configured to determine whether the road surface is wet or dry on the basis of a spatial change in luminance of pixels in a continuous region included in the image.

An imaging system of the present disclosure comprises a temperature detector and an imaging apparatus. The temperature detector is configured to measure a temperature of a road surface. The imaging apparatus comprises a camera and a road surface state determination apparatus. The road surface state determination apparatus comprises an acquisition interface and a controller. The acquisition interface is configured to acquire an image representing a road surface imaged by the camera and a signal related to the temperature of the road surface. The controller is configured to determine whether the road surface is wet or dry on the basis of a luminance of pixels included in the image and to determine whether the road surface is frozen on the basis of the signal related to the temperature of the road surface.

A road surface state determination method of the present disclosure comprises acquiring, using an acquisition interface, an image representing a road surface imaged by a camera. The road surface state determination method comprises determining, using a controller, whether the road surface is wet or dry on the basis of a spatial change in luminance of pixels in a continuous region included in the image.

BRIEF DESCRIPTION OF THE DRAWINGS

In the accompanying drawings:

FIG. 4 illustrates a non-vibration component of luminance;

FIG. 9 is a flowchart illustrating a detailed procedure for a dry/wet determination process in the second embodiment;

FIG. 10 is a functional block diagram illustrating the schematic configuration of an imaging system according to a third embodiment;

FIG. 13 is a flowchart illustrating a procedure for determining the road surface state in the third embodiment.

DETAILED DESCRIPTION

A conventional method like the one described above may end up detecting external light such as sunlight, illumination light, light projected by another vehicle, or the like at the same time as detection of the reflection of the projected light. In this case, the levels are compared for light that includes not only the reflected light but also the external light, which may prevent the road surface state from being determined accurately.

The road surface state determination apparatus, imaging apparatus, imaging system, and road surface state determination method of the present disclosure allow the state of the road surface to be determined more accurately.

First Embodiment

The first embodiment of the present disclosure is now described with reference to the drawings.

Figure 1:
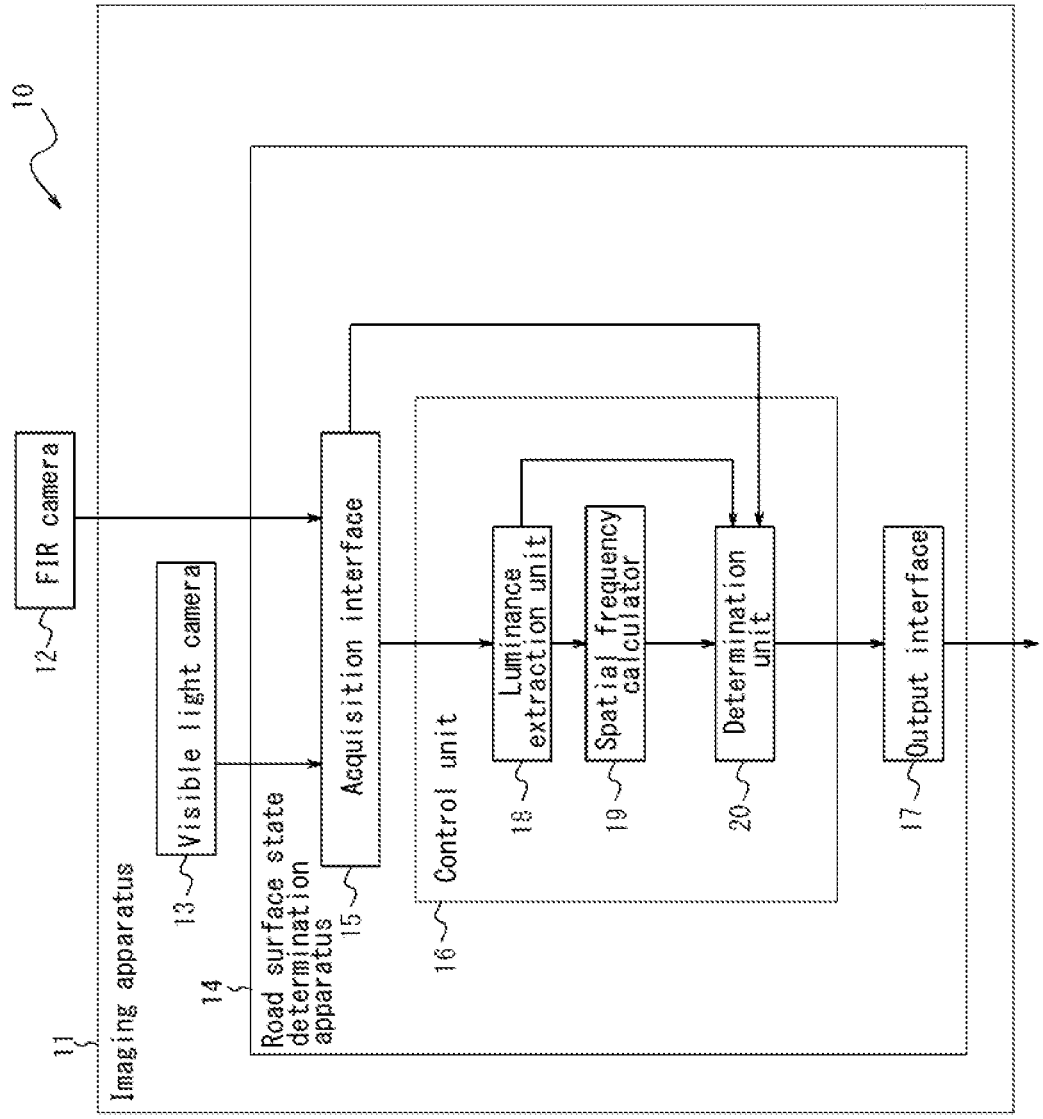
FIG. 1 is a functional block diagram illustrating the schematic configuration of an imaging system according to a first embodiment.

As illustrated in FIG. 1, an imaging system 10 is configured to include an imaging apparatus 11 and a far infrared (FIR) camera 12. The imaging apparatus 11 is configured to include a visible light camera 13 and a road surface state determination apparatus 14.

The FIR camera 12 captures infrared light emitted by the surface of a subject, generates a far infrared image of the subject, and transmits the image to the road surface state determination apparatus 14 as a signal related to the temperature of the subject, i.e. the temperature of the road surface. In the present embodiment, the subject of the FIR camera 12 is the road surface. Furthermore, the direction in which the FIR camera 12 images the road surface as the subject is the same as the direction in which the visible light camera 13 images the road surface. The imaging area of the FIR camera 12 is assumed to include the imaging area of the visible light camera 13. The imaging area of the FIR camera 12 and the imaging area of the visible light camera 13 are described below as being identical.

Instead of including the FIR camera 12, the imaging system 10 may acquire a signal related to the temperature of the road surface from a thermometer, temperature sensor, or the like for measuring the temperature of the road surface. The component for measuring the temperature of the road surface, such as the FIR camera 12, thermometer, or temperature sensor, is referred to as a "temperature detector".

Figure 2A:
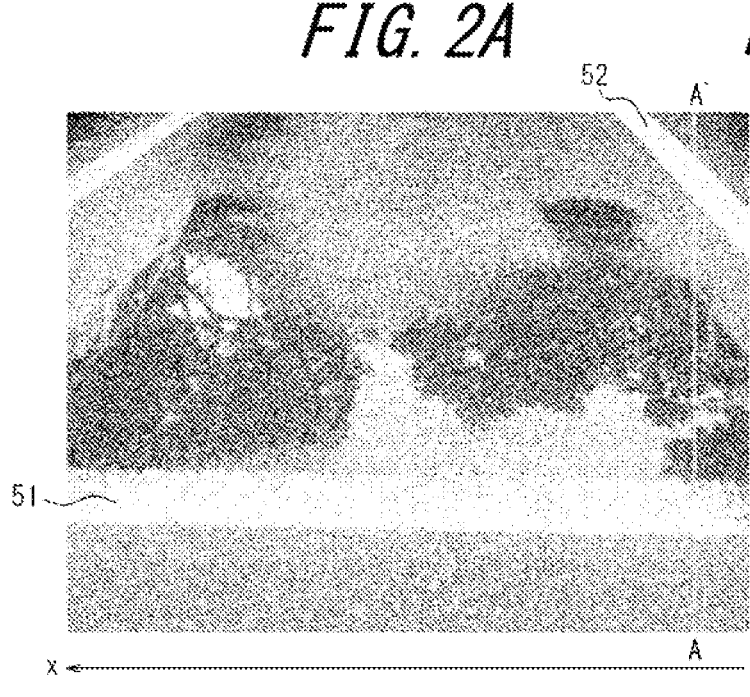
FIGS. 2A and 2B illustrate an image acquired by an acquisition interface, with FIG. 2A illustrating an example captured image of a wet road surface, and FIG. 2B illustrating the luminance along the AA' line in the image in FIG. 2A.
Figure 2B:
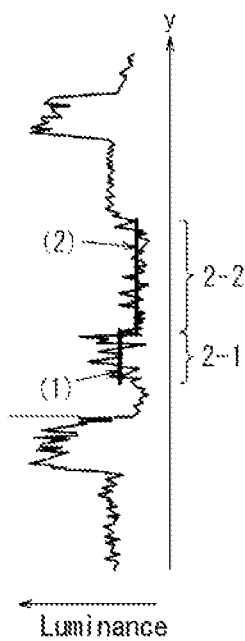

The visible light camera 13 is preferably a CCD camera or a CMOS camera. In the present embodiment, the road surface is imaged as a subject, and a visible image is generated with visible light as an image of the surface of the subject. The visible light camera 13 may image the road surface as the subject in any direction. The visible light camera 13 is described below as being attached to the front of the vehicle and imaging the road surface in the direction of vehicle travel. In the captured image, the x-axis lies in the horizontal direction of the visible image, and the y-axis lies in a direction orthogonal to the x-axis, as illustrated in FIGS. 2A and 2B. In real space, the x-axis corresponds to the left-right direction of the vehicle, and the y-axis corresponds to the travel direction of the vehicle and the up-down direction. The same holds for FIGS. 3A, 3B, 11A, 11B, 12A, and 12B. A monochrome camera may be used as the visible light camera 13. Instead of including the visible light camera 13, the imaging system 10 may also use a near infrared camera that has sensitivity in the near infrared region (NIR). The term "camera" is used simply to refer to either of the visible light camera 13 and the near infrared camera.

The road surface state determination apparatus 14 determines the dry/wet state of the road surface, i.e. whether the road surface is wet or dry, on the basis of the visible image generated by the visible light camera 13 imaging the road surface. The road surface state determination apparatus 14 also determines the frozen state of the road surface, i.e. whether the road surface is frozen, on the basis of a far infrared image generated by the FIR camera 12 capturing infrared light reflected from the road surface. The road surface state determination apparatus 14 is configured to include the functional blocks of an acquisition interface 15, a control unit 16 as a controller, and an output interface 17.

The acquisition interface 15 is an input interface of the road surface state determination apparatus 14. The acquisition interface 15 acquires a visible image from the visible light camera 13 in accordance with the imaging signal transmission format of the visible light camera 13. The acquisition interface 15 also acquires a far infrared image from the FIR camera 12 in accordance with the imaging signal transmission format of the FIR camera 12. Furthermore, the acquisition interface 15 delivers the acquired visible image and far infrared image to the control unit 16.

The control unit 16 is the portion of the road surface state determination apparatus 14 that executes various arithmetic processing and may be configured to include a general-purpose central processing unit (CPU) that executes processing in accordance with a software program and/or an application specific integrated circuit (ASIC) designed for image processing, a field-programmable gate array (FPGA), or the like. The control unit 16 is configured to include the functional blocks of a luminance extraction unit 18, a spatial frequency calculator 19, and a determination unit 20.

Next, each constituent element of the control unit 16 is described.

From a visible image acquired by the visible light camera 13, the luminance extraction unit 18 extracts the luminance of pixels along one line segment (continuous region) in the visible image. In the present embodiment, the line segment is parallel to the y-axis direction in the image space of the visible image in FIG. 2A and FIG. 3A and has end points on the edges of the image. However, the line segment is not limited to this example and may, for example, be a line segment that is parallel or inclined with respect to the x-axis. The luminance extraction unit 18 may also extract the luminance of pixels on a curve or in a plane instead of in a line segment.

For example, when the line segment for extracting luminance is the AA' line in the example visible image in FIG. 2A, then FIG. 2B represents a luminance graph in which the height y from point A in the image is plotted along the vertical axis and the luminance of each pixel is plotted along the horizontal axis.

The luminance extraction unit 18 calculates a non-vibration component from the luminance graph as follows. The non-vibration component indicates the variation in overall luminance height, excluding the luminance vibration component caused by the shape of the road surface. In general, the road has a similar brightness when the road surface is dry, i.e. the luminance is within a predetermined range, except in the portion corresponding to the lane markings 51, 52, such as the road center line or lane boundaries. When the road surface is wet and covered in rainwater, however, a reflection of surrounding objects (buildings, trees, vehicles, people, and the like) and the sky may appear in the wet region of the road surface, as illustrated in FIG. 2A. In this case, the average luminance height in a region in which the sky is reflected, for example, is higher than the average luminance height in other regions, as indicated by the bold line (1) in FIG. 2B. The average luminance in a region in which objects such as trees are reflected is lower than the average luminance in other regions, as indicated by the bold line (2) in FIG. 2B. The luminance waveform appearing in the luminance graph has a vibration component due to the spatial frequency caused by unevenness on the road surface. The luminance extraction unit 18 therefore calculates the non-vibration component as the result of removing, from the luminance graph, a vibration component with a shorter period than the period caused by unevenness on the road surface.

The non-vibration component of luminance is described with reference to FIG. 4. The broken line in FIG. 4 is an enlarged representation of some of the luminance values from the portion indicated by 2-2 in FIG. 2B. For example, the non-vibration component is the average of the luminance values in the range of one period of vibration (see $L_{ave}$ in FIG. 4), such as the period indicated between the two dashed lines. The average of the luminance values in each of the other periods is similarly taken as the non-vibration component to calculate the non-vibration component of luminance representing the variation in average height of luminance excluding the vibration component, as indicated by the bold line (2) in FIG. 2B. The non-vibration component is calculated similarly for portions other than the one indicated by 2-2 in FIG. 2B. Along with the extracted luminance of each pixel on the line segment, the luminance extraction unit 18 delivers these non-vibration components of luminance to the determination unit 20.

The non-vibration component of luminance described here is an example of an amount representing the height excluding the vibration component of the varying luminance value. The processes below may also be performed using any other amount that represents the height of the luminance value.

The spatial frequency calculator 19 calculates a spatial frequency on the basis of the luminance, extracted by the luminance extraction unit 18, of a pixel group.

Here, the relationship between the state of the road surface and the spatial frequency is explained in detail. As described above, the road surface is formed to have minute unevenness so as to have a coefficient of friction of a predetermined value or higher. A dry region of the road surface thus has minute unevenness, and the luminance changes easily. Because the road surface is covered by rainwater in a wet region of the road surface, the luminance distribution of the surface is smooth. Therefore, the spatial frequency of the luminance of pixels representing a dry region of the road surface is higher than the spatial frequency for a wet region.

Figure 3A:
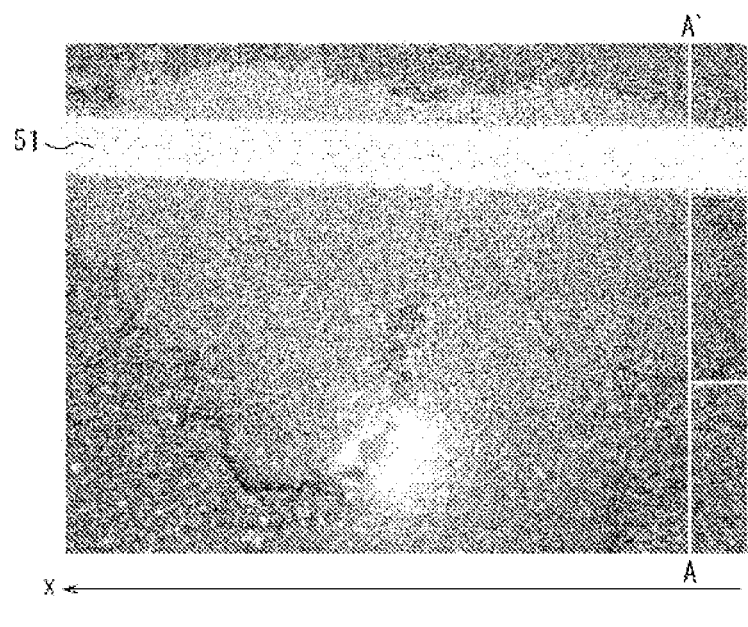
FIGS. 3A and 3B illustrate another image acquired by the acquisition interface, with FIG. 3A illustrating an example captured image of a road surface, and FIG. 3B illustrating the luminance along the AA' line in the image in FIG. 3A.
Figure 3B:
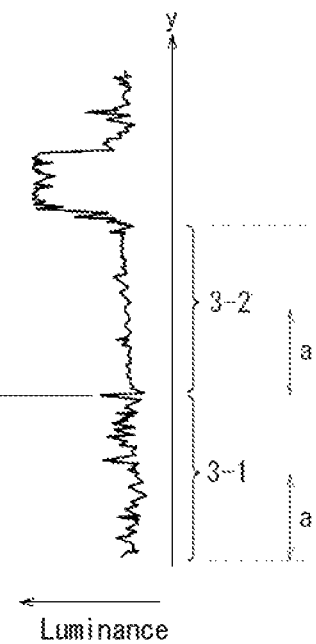

The spatial frequency is observed as a change in a parameter corresponding to the spatial frequency ("spatial frequency parameter"). The spatial frequency parameter is, for example, the number of vibration peaks per unit length when observing the vibration of an image signal along the line segment from which pixels are extracted. The spatial frequency parameter may also be the number of times per unit length that the waveform of the pixel signal cuts across the above-described non-vibration component of luminance from above to below or from below to above. Referring now to FIGS. 3A and 3B, the road surface is dry in the region indicated by 3-1 along the AA' line in the visible image illustrated in FIG. 3A, whereas the road surface is wet in the region indicated by 3-2. Hence, as illustrated in FIG. 3B, the spatial frequency parameter for the portion indicated in 3-1 is higher than the spatial frequency parameter for the portion indicated in 3-2.

In other words, it is clear that along one line segment in a region other than the lane marking 51 in the image, the spatial frequency is continuously within a predetermined range in two or more portions (see 3-1 and 3-2 in FIG. 3B). It is also clear that among the two or more portions, a first region composed of pixels with the higher spatial frequency parameter is dry, whereas a second region composed of pixels with the lower spatial frequency parameter is wet.

The spatial frequency calculator 19 may convert the spatial region represented by the pixel signal into a spatial frequency region and calculate the frequency that yields the peak value as the spatial frequency. In this case, the calculated spatial frequency itself can be used as the spatial frequency parameter.

The determination unit 20 performs a dry/wet determination process to determine whether the road surface is wet or dry on the basis of a spatial change in the luminance of the pixel values in a continuous region included in the image. The spatial change is a change in the image space of a characteristic amount related to the image, such as the luminance of each pixel and the non-vibration component of luminance on a line segment as acquired by the luminance extraction unit 18, the spatial frequency parameter acquired from the spatial frequency calculator 19, or the like.

In the dry/wet determination process, the determination unit 20 first performs a first determination process to determine a dry region and a wet region appearing in the image on the basis of the spatial frequency parameter calculated by the spatial frequency calculator 19.

In the first determination process, the determination unit 20 extracts each frequency continuous portion in which the spatial frequency parameter is continuously within a predetermined range across at least a predetermined number a of pixels. Here, the predetermined number a of pixels is the value expected to be appropriate for determining the road surface state when the spatial frequency is continuously within a predetermined range across at least this number of pixels. In other words, the predetermined number a of pixels is considered to be the value such that when the spatial frequency is continuous across a range that is smaller than this value, the determination of the road surface state cannot be appropriately made due to the inclusion of noise. The predetermined number a of pixels may be set to an appropriate value, such as 10 pixels.

The determination unit 20 compares the spatial frequency parameter, calculated as described above, in each of the extracted plurality of frequency continuous portions. When the difference between a plurality of spatial frequency parameters is a predetermined value or greater, the determination unit 20 determines that the first region (3-1 in FIG. 3A) composed of pixels with the higher spatial frequency parameter is dry. The determination unit 20 determines that the second region (3-2 in FIG. 3A) composed of pixels with the lower spatial frequency parameter is wet. Here, the predetermined value is a value allowing the determination that a dry region and a wet region are included in the road surface when the difference in spatial frequency is at least this value. Specifically, the predetermined value is empirically the smallest of the differences between the spatial frequency parameters that have been calculated for dry regions and the spatial frequency parameters that have been calculated for wet regions. This predetermined value may be set to an appropriate value, such as a value corresponding to 30% of the lower spatial frequency.

In the dry/wet determination process, the determination unit 20 performs a second determination process to determine whether there is a wet region on the road surface appearing in the image on the basis of the non-vibration component of luminance extracted by the luminance extraction unit 18.

In the second determination process, the determination unit 20 extracts luminance continuous portions (see 2-1, 2-2 in FIG. 2B) in which the non-vibration component of the luminance of pixels along a line segment, as extracted by the luminance extraction unit 18, is continuously within a predetermined range. The determination unit 20 compares the non-vibration component of luminance in each of a plurality of extracted luminance continuous portions. When the difference in the non-vibration component of luminance is a predetermined value or greater, the determination unit 20 further determines that at least a portion of the road surface appearing in the image for the second determination process is wet. Here, the predetermined value is a value allowing the determination that a wet region is included in the road surface when the difference in the non-vibration component is at least this value. This predetermined value may be set to an appropriate value, such as a value corresponding to 30% of the lower non-vibration component.

In terms of the example image in FIGS. 2A and 2B, the sky is reflected on the water surface in the region indicated by 2-1 on the AA' line in FIG. 2A, causing the non-vibration component of luminance for the portion corresponding to 2-1 in FIG. 2B to be higher than the non-vibration component of luminance for the other portions. A tree is reflected on the water surface in the region corresponding to 2-2 on the AA' line in FIG. 2A, causing the non-vibration component of luminance for the portion corresponding to 2-2 in FIG. 2B to be lower than the non-vibration component for the other portions.

In other words, the determination unit 20 determines that there is a wet region on the road surface appearing in the image when a region other than the lane markings 51, 52 in the image satisfies the following two conditions. The first condition is that along one line segment, the non-vibration component of luminance is continuous within a predetermined range in two or more portions (see 2-1 and 2-2 in FIG. 2B). The second condition is that the difference in the continuous non-vibration components is a predetermined value or greater.

When it is determined whether a region of the road surface appearing in the visible image is wet, the determination unit 20 also performs a frozen determination process to determine whether the region is frozen, as mentioned above.

Specifically, the determination unit 20 determines whether the temperature of the road surface from the far infrared image generated by the FIR camera 12 is a predetermined temperature or higher for the region of the road surface determined to be wet on the basis of the visible image. When it is determined that the temperature of the road surface is the predetermined temperature or higher, it is determined that the region of the road surface is wet and is not frozen. When it is determined that the temperature of the road surface is lower than the predetermined temperature, it is determined that the region of the road surface is wet and frozen. The predetermined temperature is the critical temperature at which rainwater covering the road surface changes from a liquid to a solid and is preferably set to be approximately from −2° C. to 0° C.

The determination unit 20 also determines whether the temperature of the road surface indicated by the far infrared image is a predetermined temperature or higher for the region of the road surface determined to be dry on the basis of the visible image. When it is determined that the temperature of the road surface is the predetermined temperature or higher, it is determined that the region of the road surface is dry and is not frozen. When it is determined that the temperature of the road surface is lower than the predetermined temperature, it is determined that the region of the road surface is dry and is frozen.

When the determination unit 20 has determined whether at least a portion of the road surface is wet in the dry/wet determination process, the determination unit 20 determines whether the temperature of the road surface is a predetermined temperature or higher. The determination unit 20 determines that the road surface is not frozen when the temperature of the road surface is a predetermined temperature or higher. The determination unit 20 determines that the road surface is frozen when the temperature of the road surface is lower than a predetermined temperature.

The control unit 16 has been described as performing processing on pixels that are along the AA' line as one line segment, but in order to perform processing on all of the pixels in a predetermined range of the image, the control unit 16 performs the same processing while sequentially shifting the AA' line. In this case, the predetermined range of the image is a region in which the road surface state is determined by the control unit 16 as being continuous on the basis of the spatial change in the luminance of the pixels. The control unit 16 may perform processing on pixels in the predetermined range of the image at any interval. In this case, the control unit 16 performs processing while shifting the AA' line by any interval.

When the direction of the AA' line is in the x-direction, i.e. in the lateral direction of the vehicle in real space, then the interval by which the AA' line is shifted may be decreased as the AA' line draws closer to the vehicle in which the visible light camera 13 and the FIR camera 12 are mounted. The vehicle or the driver can obtain information immediately applicable for driving by the road surface state being determined to a higher degree of accuracy for close regions than for far regions of the road surface being driven on.

Instead of acquiring a far infrared image from the FIR camera 12, the road surface state determination apparatus 14 may acquire a signal representing the temperature from a thermometer or a temperature sensor. In this case, the road surface state determination apparatus 14 makes the above determination of whether the road surface is frozen on the basis of the temperature of the road surface acquired by the thermometer or the temperature sensor.

The output interface 17 is an output interface of the road surface state determination apparatus 14. The output interface 17 outputs the road surface state determined by the control unit 16 to a display apparatus, a vehicle control apparatus, or the like connected to the road surface state determination apparatus 14.

Figure 5:
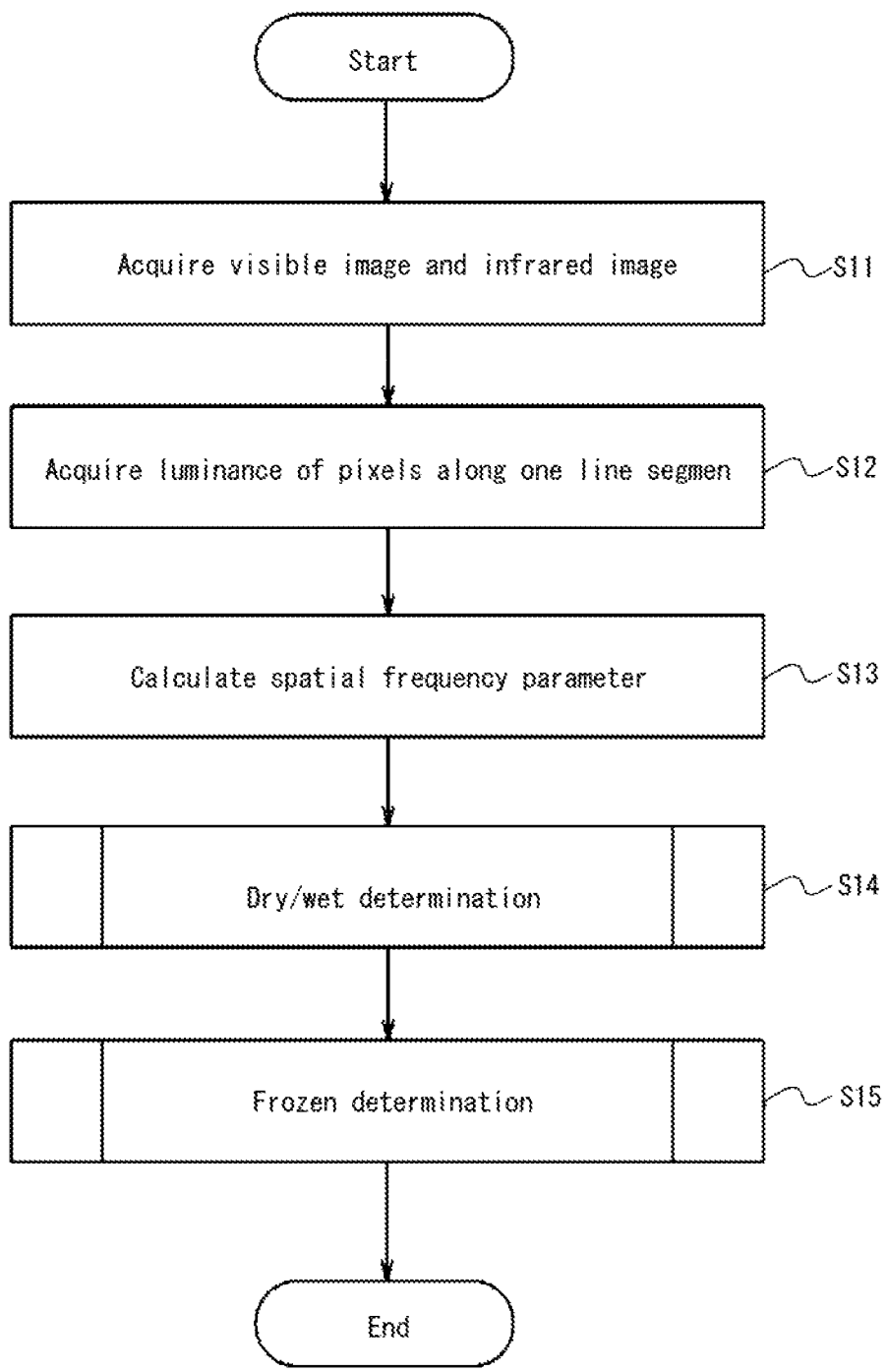
FIG. 5 is a flowchart illustrating a procedure for determining the road surface state in the first embodiment.

Using the flowchart in FIG. 5, a road surface state determination method of the road surface state determination apparatus 14 according to the first embodiment is described.

First, the acquisition interface 15 acquires a captured visible image of the road surface from the visible light camera 13 and acquires a captured far infrared image of infrared light emitted by the road surface from the FIR camera 12 (step S11).

When the visible image is acquired in step S11, the luminance extraction unit 18 extracts the luminance of pixels along one line segment within the visible image (step S12). The spatial frequency calculator 19 calculates the spatial frequency parameter for the luminance, extracted by the luminance extraction unit 18, of pixels on the line segment (step S13).

Figure 6:
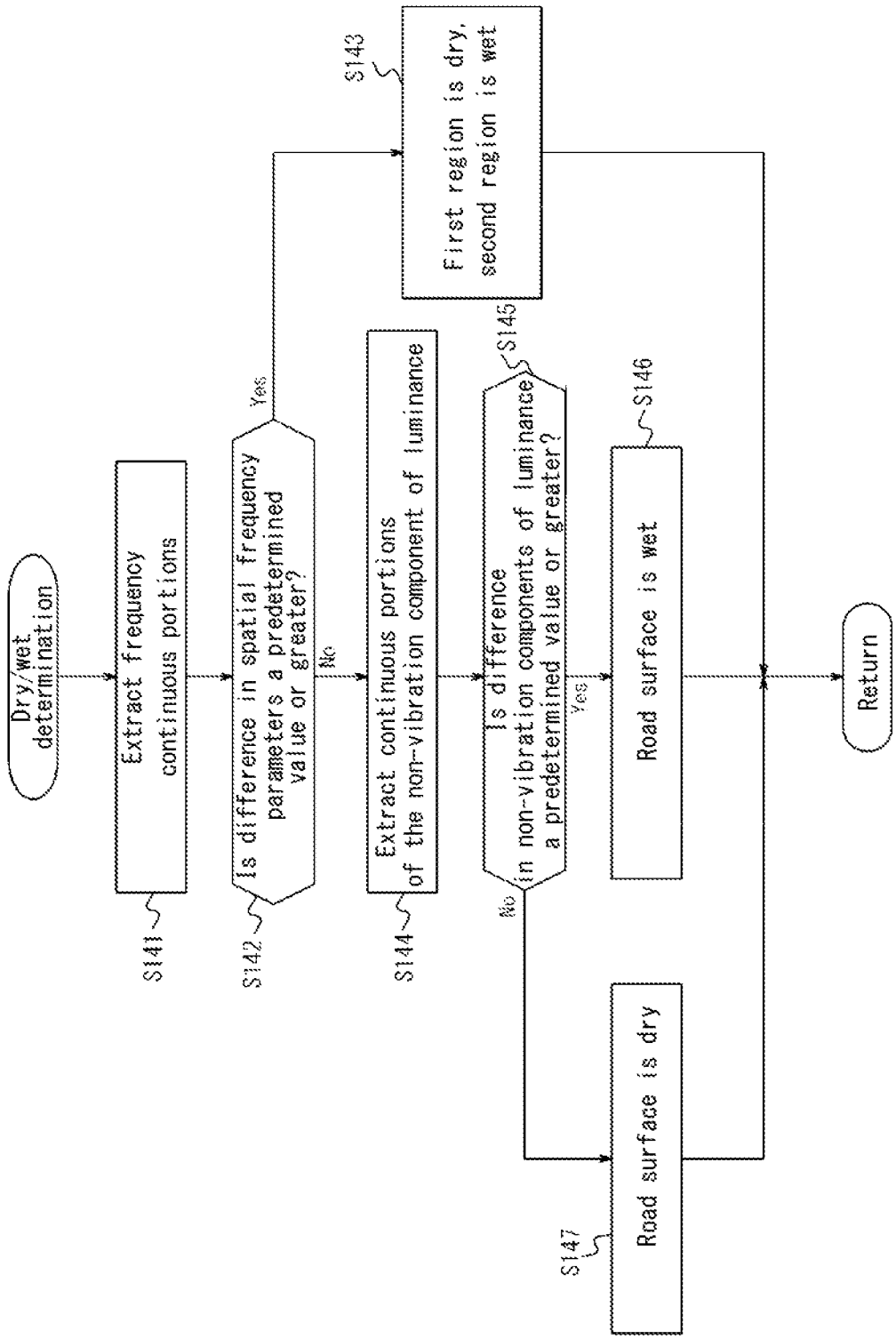
FIG. 6 is a flowchart illustrating a detailed procedure for a dry/wet determination process in the first embodiment.

Next, the determination unit 20 performs the dry/wet determination process on the basis of the spatial frequency parameter calculated by the spatial frequency calculator 19 (step S14). In the dry/wet determination process, the determination unit 20 first performs the first determination process by extracting frequency continuous portions in which the spatial frequency parameter is continuously within a predetermined range across at least a predetermined number a of pixels, as illustrated in FIG. 6 (step S141). The determination unit 20 then determines whether the difference between the spatial frequency parameters in the plurality of frequency continuous portions extracted in step S141 is a predetermined value or greater (step S142).

In step S142, when the difference between the plurality of spatial frequency parameters is the predetermined value or greater, the determination unit 20 determines that the first region composed of pixels with the higher spatial frequency parameter is dry, whereas the second region composed of pixels with the lower spatial frequency parameter is wet (step S143).

Subsequently, the determination unit 20 performs the second determination process in the dry/wet determination process when it was determined, in step S142, that the difference between spatial frequency parameters was less than the predetermined value. In the second determination process, the determination unit 20 extracts luminance continuous portions in which the non-vibration component of the luminance of pixels along a line segment, as extracted by the luminance extraction unit 18, is continuously within a predetermined range (step S144). The determination unit 20 then determines whether the difference between the non-vibration components of the extracted luminance continuous portions is a predetermined value or greater (step S145). When the difference between the non-vibration components is the predetermined value or greater, the determination unit 20 determines that at least a portion of the road surface appearing in the image is wet (step S146).

When the difference between the non-vibration components is less than the predetermined value, the determination unit 20 determines that the road surface appearing in the image is dry (step S147).

Subsequently, returning to FIG. 5, the determination unit 20 performs the frozen determination process to determine whether the region of the road surface determined in step S14 to be wet or dry is frozen (step S15).

Figure 7:
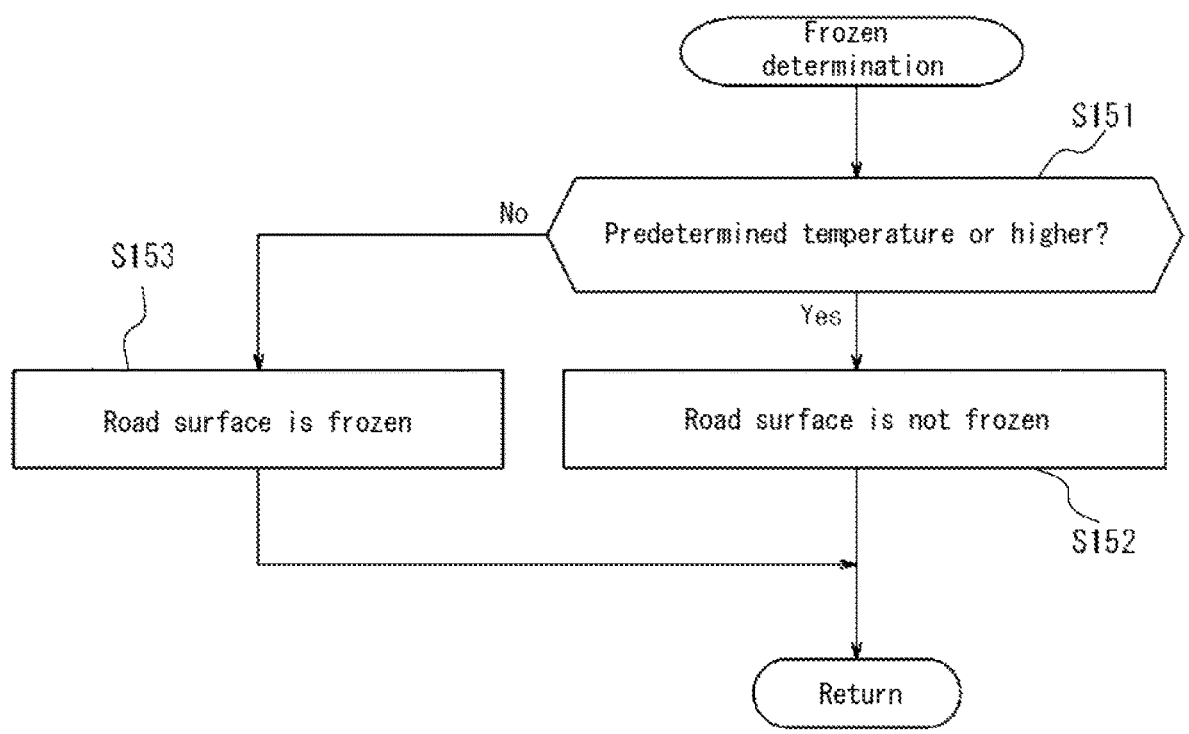
FIG. 7 is a flowchart illustrating a detailed procedure for a frozen determination process in the first embodiment.

In the frozen determination process, the determination unit 20 determines whether the temperature from the far infrared image generated by the FIR camera 12 is a predetermined temperature or higher for the region of the road surface determined to be wet, as illustrated in FIG. 7 (step S151). When it is determined that the temperature is the predetermined temperature or higher, the determination unit 20 determines that the region of the road surface is wet and is not frozen (step S152). When it is determined that the temperature is lower than the predetermined temperature, the determination unit 20 determines that the region of the road surface is wet and is frozen (step S153).

Similarly, the determination unit 20 performs the process in step S151 for the dry region of the road surface. In this case, when it is determined that the temperature is the predetermined temperature or higher, the determination unit 20 determines that the region of the road surface is dry and is not frozen (step S152). When it is determined that the temperature is lower than the predetermined temperature, the determination unit 20 determines that the region of the road surface is dry and is frozen (step S153).

The determination unit 20 also performs the frozen determination process to determine freezing of the road surface for which the determination of whether a portion of the road surface is wet was made (step S15). As this frozen determination process is similar to the aforementioned determination process, a detailed explanation is omitted.

As described above, the determination unit 20 in the first embodiment determines the state of the road surface, specifically whether the road surface is wet, on the basis of the luminance of pixels included in a visible image. Unlike a known method to determine the road surface state using the reflection of light projected from the vehicle, this method can avoid problems such as accurate determination being prevented by the effect of external light. This method can therefore determine the state of the road surface accurately.

The determination unit 20 of the first embodiment determines a wet region and a dry region of the road surface on the basis of the spatial frequency parameter related to the spatial frequency of luminance. Consequently, the determination unit 20 can determine whether a region is a dry region in which the luminance tends to change due to minute unevenness. i.e. a region with a characteristically high spatial frequency parameter, or a wet region in which the luminance distribution of the road surface is smooth because the surface is covered in rainwater, i.e. a region with a characteristically low spatial frequency parameter, on the basis of a quantitative index using a characteristic of an image representing the road surface.

In the first embodiment, luminance continuous portions in which the non-vibration component of the extracted luminance of pixels along a line segment is continuously within a predetermined range are extracted, and a plurality of luminance continuous portions are compared to determine whether the road surface is wet. In other words, it is determined that the road surface is wet when the luminance values differ due to objects or the sky being reflected by rainwater. Hence, the road surface can also be accurately determined to be wet when the luminance distribution is not smooth due to the surrounding environment being reflected in the rainwater.

In the first embodiment, it is determined whether the road surface is frozen on the basis of a far infrared image. It is thus possible to learn not only the dry/wet state of the road surface, but also whether each of a dry region and a wet region of the road surface is frozen. Outputting this information to the vehicle control system or the like makes it possible to alert the driver more severely or to support driving to prevent slipping when, for example, the vehicle or the like is passing through a region that is wet and frozen, rather than simply a wet region.

Second Embodiment

An imaging system 30 according to a second embodiment of the present disclosure is now described with reference to the drawings. Functional blocks that are the same as the imaging system 10 in the first embodiment are labeled with the same reference signs, and a description thereof is omitted as appropriate.

Figure 8:
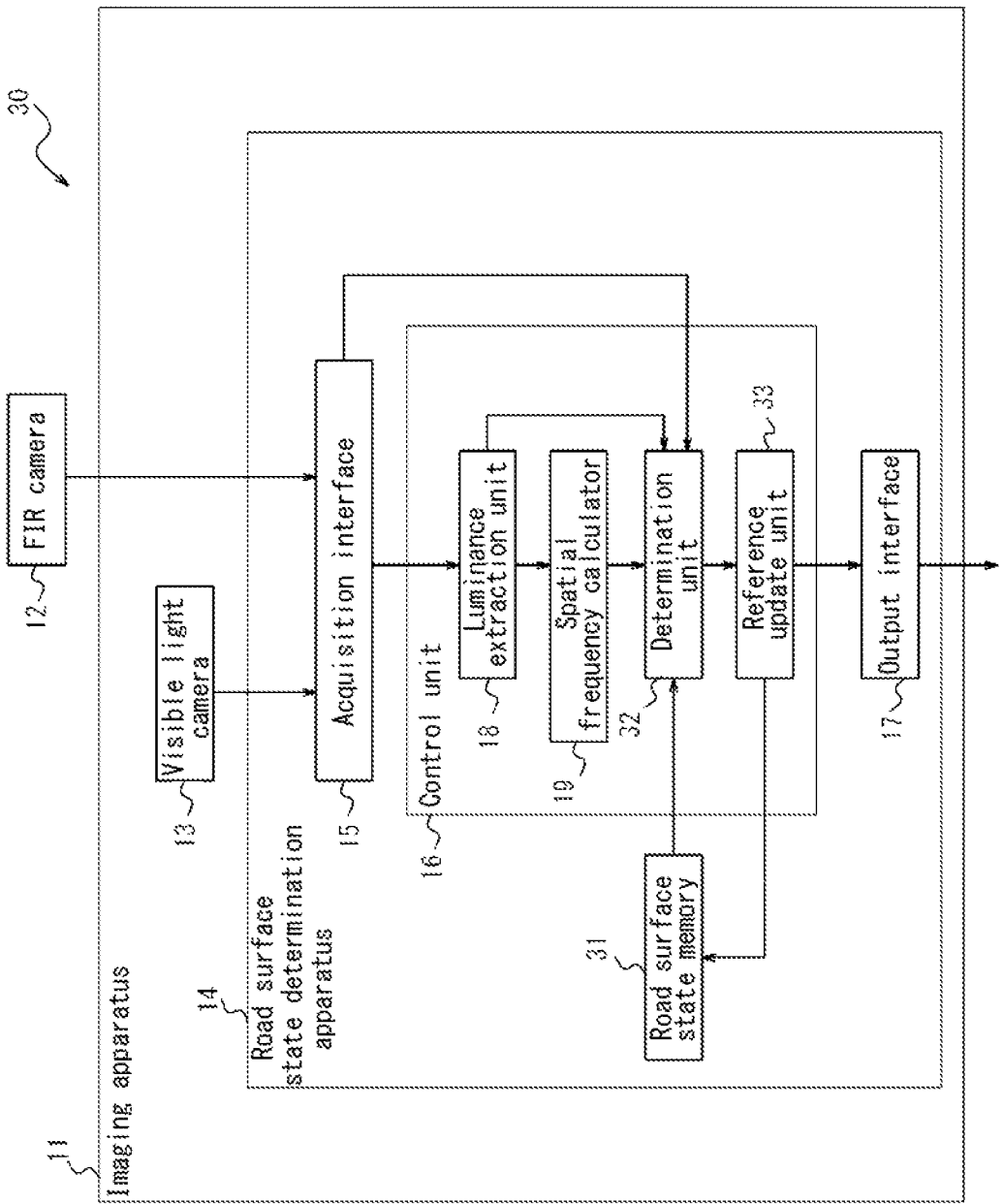
FIG. 8 is a functional block diagram illustrating the schematic configuration of an imaging system according to a second embodiment.

As illustrated in FIG. 8, the imaging system 30 in the second embodiment is configured to include an imaging apparatus 11 and a FIR camera 12, like the imaging system 10 in the first embodiment. The imaging apparatus 11 is also configured to include a visible light camera 13 and a road surface state determination apparatus 14. The road surface state determination apparatus 14 is configured to include the functional blocks of an acquisition interface 15, a road surface state memory 31, a control unit 16, and an output interface 17.

The road surface state memory 31 includes a rewritable memory for storing a reference luminance and a reference spatial frequency parameter.

The reference luminance is the most frequently occurring luminance in an image, captured by the imaging apparatus 11, of a road surface for which the control unit 16 makes the determination of whether the road surface is wet, i.e. among the luminance values of pixels forming an image captured in a period of time immediately before the control unit 16 makes the determination. This reference luminance is the luminance of pixels representing a dry road surface under the assumption that the majority of the road surface is dry and a portion is wet.

The reference spatial frequency parameter is the most frequently occurring spatial frequency parameter among the spatial frequency parameters of an image, captured by the imaging apparatus 11, of a road surface for which the control unit 16 makes the determination of whether the road surface is wet. The captured image of the road surface for which the control unit 16 makes the determination of whether the road surface is wet is an image captured in a period of time immediately before the control unit 16 makes the determination. This reference spatial frequency parameter is the spatial frequency parameter of a dry region of the road surface under the assumption that the majority of the road surface is dry and a portion is wet.

The rewritable memory can, for example, be a nonvolatile memory, such as a flash memory, a magnetoresistive random access memory (MRAM), a ferroelectric random access memory (FeRAM), or the like.

The control unit 16 is configured to include the functional blocks of a luminance extraction unit 18, a spatial frequency calculator 19, a determination unit 32, and a reference update unit 33. The processing by the determination unit 32 in the second embodiment differs from the processing by the determination unit 20 in the first embodiment.

The determination unit 32 extracts a frequency continuous portion in which the spatial frequency parameter, calculated by the spatial frequency calculator 19, is continuously within a predetermined range across at least a predetermined number a of pixels (see 3-1 and 3-2 in FIG. 3B). The determination unit 32 compares the spatial frequency parameter in the extracted frequency continuous portion with the reference spatial frequency parameter stored in the road surface state memory 31.

When the difference between the spatial frequency parameter and the reference spatial frequency parameter is a predetermined value or greater, the determination unit 32 determines that the region of the road surface corresponding to the frequency continuous portion is wet. When the difference between the spatial frequency parameter and the reference spatial frequency parameter is less than the predetermined value, the determination unit 32 performs the below-described determination based on the luminance for a region of the road surface appearing in the image.

The determination unit 32 extracts a luminance continuous portion in which the non-vibration component of the luminance of pixels along the AA' line, as extracted by the luminance extraction unit 18, is continuously within a predetermined range. The determination unit 32 then compares the non-vibration component of luminance in the extracted luminance continuous portion with the reference non-vibration component stored in the road surface state memory 31. When the difference between the non-vibration component of luminance and the reference non-vibration component is a predetermined value or greater, the determination unit 32 determines that the region of the road surface corresponding to the luminance continuous portion is wet. When the difference between the non-vibration component of luminance and the reference non-vibration component is less than the predetermined value, the determination unit 32 determines that the region of the road surface corresponding to the luminance continuous portion is dry.

Like the determination unit 20 of the first embodiment, the determination unit 32 performs a frozen determination process, to determine whether the road surface is frozen, after the determination of the dry/wet state of the road surface. As the frozen determination process by the determination unit 32 is identical to the frozen determination process by the determination unit 20 of the first embodiment, a detailed explanation is omitted.

The reference update unit 33 stores the most frequently occurring luminance, among the luminance values of pixels forming an image captured by the imaging apparatus 11 in a period of time during travel down the same road, in the road surface state memory 31 as the reference luminance. The reference update unit 33 also stores the most frequently occurring spatial frequency parameter, among the spatial frequency parameters calculated from an image captured by the imaging apparatus 11 in a period of time during travel down the same road, in the road surface state memory 31 as the reference spatial frequency parameter.

The road surface state determination method of the road surface state determination apparatus 14 according to the second embodiment is basically the same as the road surface state determination method of the road surface state determination apparatus 14 according to the first embodiment, but the dry/wet determination process differs. The dry/wet determination process in the second embodiment is described below.

The first determination process of the dry/wet determination process in the second embodiment is first described. In the first determination process, the determination unit 32 extracts frequency continuous portions in which the spatial frequency parameter is continuously within a predetermined range across at least a predetermined number a of pixels, as illustrated in FIG. 9 (step S241). The determination unit 32 then determines whether the difference between the spatial frequency parameters in the plurality of frequency continuous portions extracted in step S241 and the reference spatial frequency parameter is a predetermined value or greater (step S242).

When the difference between a spatial frequency parameter and the reference spatial frequency parameter is the predetermined value or greater in step S242, the determination unit 32 determines that the region composed of pixels pertaining to that spatial frequency parameter is wet (step S243).

When the difference between the spatial frequency parameter and the reference spatial frequency parameter is less than the predetermined value in step S242, the determination unit 32 performs the second determination process.

In the second determination process, the determination unit 32 extracts a luminance continuous portion in which the non-vibration component of the luminance of pixels along a line segment, as extracted by the luminance extraction unit 18, is continuously within a predetermined range (step S244). The determination unit 20 then determines whether the difference between the non-vibration component of luminance in the extracted luminance continuous portion and the reference non-vibration component is a predetermined value or greater (step S245). When the difference between the non-vibration component of luminance and the reference non-vibration component is the predetermined value or greater, the determination unit 32 determines that the road surface is wet (step S246).

When the difference between the non-vibration component of luminance and the reference non-vibration component is less than the predetermined value, the determination unit 32 determines that the road surface is dry (step S247).

As described above, the determination unit 32 of the second embodiment determines the state of the road surface on the basis of the reference spatial frequency parameter, which is considered to be the spatial frequency parameter of a dry region. The most frequently occurring spatial frequency parameter among the spatial frequency parameters of a captured image in a period of time during travel down the same road is taken to be the reference spatial frequency parameter. For a road surface that is mostly dry but that does include a wet portion, the dry region of the road surface can therefore be accurately determined.

Third Embodiment

An imaging system 40 according to a third embodiment of the present disclosure is now described with reference to the drawings. Functional blocks that are the same as the imaging system 10 in the first embodiment and the imaging system 30 in the second embodiment are labeled with the same reference signs, and a description thereof is omitted as appropriate.

As illustrated in FIG. 10, the imaging system 40 in the third embodiment is also configured to include an imaging apparatus 11 and a FIR camera 12, like the imaging system 10 in the first embodiment. The imaging apparatus 11 is configured to include a visible light camera 13 and a road surface state determination apparatus 14. The road surface state determination apparatus 14 is configured to include the functional blocks of an acquisition interface 15, a control unit 16, and an output interface 17. The processing by the control unit 16 in the third embodiment differs from that of the control unit 16 in the first embodiment.

The control unit 16 is configured to include a lane marking detector 41 and a determination unit 42.

The lane marking detector 41 determines whether a lane marking 53 (see FIGS. 11A and 11B) can be extracted from the visible image acquired by the acquisition interface 15.

Figure 11A:
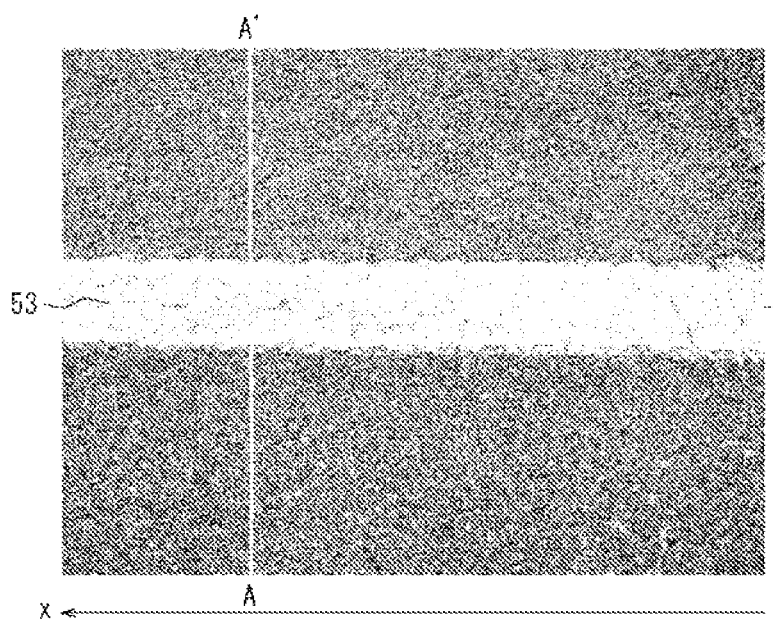
FIGS. 11A and 11B illustrate an image acquired by an acquisition interface, with FIG. 11A illustrating an example captured image of a dry road surface including a lane marking, and FIG. 11B illustrating the luminance along the AA' line in the image in FIG. 11A.
Figure 11B:
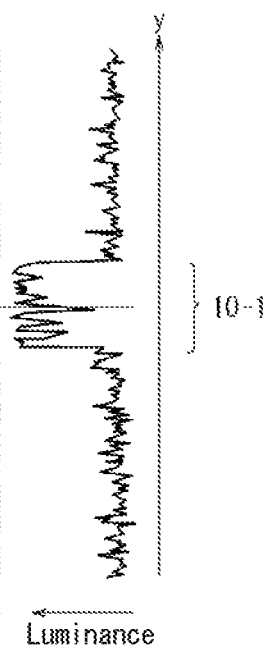

Here, the relationship between the state of the road surface and the detection of a lane marking is explained in detail. As illustrated in FIG. 11A, the lane marking 53 displayed on the road surface is typically a color such as white. The luminance of pixels in the portion corresponding to the lane marking 53, indicated by 10-1, is therefore higher, as illustrated in FIG. 11B. In this way, the pixels representing the lane marking 53 and the pixels representing the road excluding the lane marking 53 have a difference in pixel value of a predetermined value or greater, thus allowing the pixels corresponding to the edges of the lane marking 53 to be detected as edges, and approximate straight lines of the extracted edge groups to be detected as the lane marking 53.

Figure 12A:
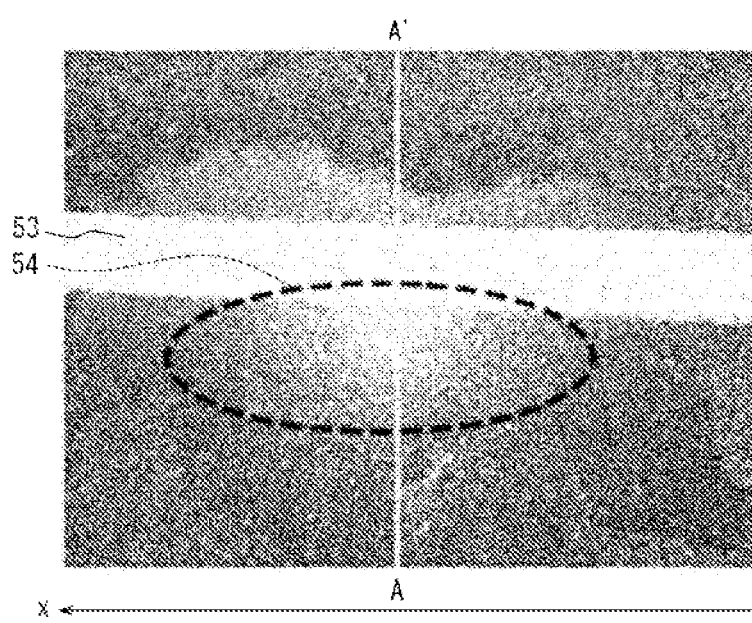
FIGS. 12A and 12B illustrate an image acquired by an acquisition interface, with FIG. 12A illustrating an example captured image of a wet road surface including a lane marking, and FIG. 12B illustrating the luminance along the AA' line in the image in FIG. 12A.
Figure 12B:
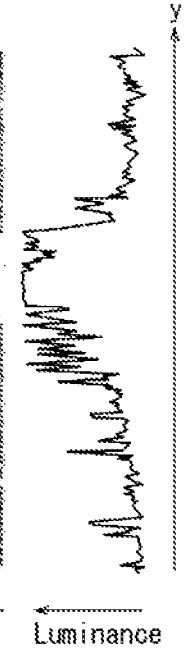

As illustrated in FIG. 12A, however, when the road surface is wet, an edge might not be detected because of a gradual change in the luminance value in a region where light is reflected due to sunlight, illumination light, or other light being reflected by rainwater covering the road surface, as in the portion 54 surrounded by the dotted line.

It can therefore be known that the road surface appearing in a visible image is wet when the lane marking 53 cannot be detected due to an edge not being detected in a region of interest in the image.

The lane marking detector 41 performs processing, on the basis of the visible image, to detect the lane marking 53 using a known lane marking detection method so as to determine whether the lane marking 53 can be detected.

Specifically, the lane marking detector 41 performs a known process for detecting edges corresponding to the edges of one lane marking 53 appearing in a predetermined region of interest in an image acquired by the acquisition interface 15. As a result of the process, when two sets of edge groups respectively approximated to two straight lines are detected, and the distance between the two straight lines corresponds to the width of the lane marking 53, then the lane marking detector 41 outputs a detection result indicating that detection of the lane marking 53 is possible. When the edges are not detected, the lane marking detector 41 outputs a detection result indicating that detection of the lane marking 53 is not possible.

When the detection result indicating that detection of the lane marking 53 is not possible is output, the determination unit 42 determines that the road surface appearing in the image is wet. When the detection result indicating that detection of the lane marking 53 is possible is output, the determination unit 42 determines that the road surface appearing in the image is dry.

Like the determination unit 20 of the first embodiment, the determination unit 42 performs a frozen determination process, to determine whether the road surface is frozen, after the determination of whether the road surface appearing in the image is wet or dry. As the frozen determination process by the determination unit 42 is identical to the frozen determination process by the determination unit 20 of the first embodiment, a detailed explanation is omitted.

Using the flowchart in FIG. 13, a road surface state determination method of the road surface state determination apparatus 14 according to the third embodiment is described.

First, the acquisition interface 15 acquires a captured visible image of the road surface from the visible light camera 13 and a captured far infrared image of infrared light emitted by the road surface from the FIR camera 12 (step S31).

Once the visible image is generated in step S31, the lane marking detector 41 performs a process for lane marking detection, using a known lane marking detection method, on the basis of the visible image and outputs a detection result indicating whether lane marking detection is possible (step S32).

When a detection result indicating that detection of the lane marking 53 is possible is output in step S32, the determination unit 42 determines that the road surface appearing in the image is dry (step S33). When a detection result indicating that detection of the lane marking 53 is not possible is output in step S32, the determination unit 42 determines that the road surface appearing in the image is wet (step S34).

Subsequently, the determination unit 42 performs a frozen determination process to determine whether the road surface determined in step S33 to be dry is frozen and whether the road surface determined in step S34 to be wet is frozen (step S35). The determination unit 42 can thereby determine if the road surface is dry and frozen, dry and not frozen, wet and frozen, or wet and not frozen. As the frozen determination process in step S35 is similar to the frozen determination process of the first embodiment, a detailed explanation is omitted.

As described above, the road surface state determination apparatus 14 of the third embodiment performs a process for detecting the lane marking 53, determines that the road surface is dry when detection of the lane marking 53 is successful, and determines that the road surface is wet when detection of the lane marking 53 is unsuccessful. By a determination thus being made on the basis of the lane marking 53, which is prescribed by law, the road surface state can be determined accurately on roads marked with lane markings 53.

Fourth Embodiment

An imaging system 10 according to a fourth embodiment of the present disclosure is now described with reference to the drawings. Functional blocks that are the same as the imaging system 10 in the first embodiment are labeled with the same reference signs, and a description thereof is omitted as appropriate.

Like the imaging system 10 of the first embodiment, an imaging system 10 of the fourth embodiment is configured to include an imaging apparatus 11 and a far infrared (FIR) camera 12, as illustrated in FIG. 1. The imaging apparatus 11 is configured to include a visible light camera 13 and a road surface state determination apparatus 14.

Like the road surface state determination apparatus 14 of the first embodiment, the road surface state determination apparatus 14 of the fourth embodiment is configured to include the functional blocks of an acquisition interface 15, a control unit 16 as a controller, and an output interface 17. Like the control unit 16 of the first embodiment, the control unit 16 of the fourth embodiment is also configured to include the functional blocks of a luminance extraction unit 18, a spatial frequency calculator 19, and a determination unit 20.

As described above, the determination unit 20 of the first embodiment determines whether a region determined to be dry is frozen and whether a region determined to be wet is frozen. In the fourth embodiment, the determination unit 20 determines whether either or both of a region determined to be dry and a region determined to be wet are frozen.

In the first embodiment, the determination unit 20 performs the frozen determination process after the dry/wet determination process, but the determination unit 20 may perform the dry/wet determination process alone without performing the frozen determination process.

REFERENCE SIGNS LIST 10, 30, 40 Imaging system
11 Imaging apparatus
12 FIR camera
13 Visible light camera
14 Road surface state determination apparatus
15 Acquisition interface
16 Control unit
17 Output interface
18 Luminance extraction unit
19 Spatial frequency calculator
20, 32, 42 Determination unit
31 Road surface state memory
41 Lane marking detector
51, 52, 53 Lane marking

The invention claimed is:

1. A road surface state determination apparatus comprising:
an acquisition interface configured to acquire an image representing a road surface imaged by a camera; and
a controller configured to determine whether the road surface is wet or dry on the basis of a spatial change in luminance of pixels in a continuous region included in the image,
wherein the controller is configured to calculate a parameter corresponding to a spatial frequency of the luminance and to determine a wet region of the road surface on the basis of the calculated parameter, and
wherein the controller is configured to extract a frequency continuous portion in which the parameter corresponding to the spatial frequency of the continuous region of the image is continuous across at least a predetermined length, and when a plurality of frequency continuous portions is extracted, to determine that the road surface is wet at the frequency continuous portion, among the extracted plurality of frequency continuous portions, in which the parameter corresponds to a lower spatial frequency.

2. The road surface state determination apparatus of claim 1, wherein the controller is configured to detect a non-vibration component that indicates variation in overall luminance height excluding a luminance vibration component caused by a shape of the road surface and to determine whether at least a portion of the road surface is wet on the basis of a change in the non-vibration component.

3. The road surface state determination apparatus of claim 2, wherein the controller is configured to extract, from among pixels included in the continuous region of the image, a luminance continuous portion in which the non-vibration component is continuous across at least a predetermined length, and when a plurality of the luminance continuous portions is extracted, to determine whether at least a portion of the road surface is wet by comparing the non-vibration components corresponding to the extracted plurality of the luminance continuous portions.

4. The road surface state determination apparatus of claim 1, wherein the controller is configured to perform a process to detect a lane marking on the road surface from a change in luminance of the pixels in the continuous region included in the image, to determine that the road surface is dry when detection of the lane marking is successful, and to determine that the road surface is wet when detection of the lane marking is unsuccessful.

5. The road surface state determination apparatus of claim 1, wherein the acquisition interface is configured to acquire, from a temperature detector configured to measure a temperature of a road surface, a signal related to the temperature of the road surface, and the controller is configured to determine whether the road surface is frozen on the basis of the signal related to the temperature of the road surface.

6. The road surface state determination apparatus of claim 5, wherein the temperature detector is a far infrared camera configured to image the road surface, and the controller is configured to determine whether a predetermined region on the road surface is frozen on the basis of a far infrared image captured by the far infrared camera.

7. An imaging apparatus comprising:
a camera; and
a road surface state determination apparatus comprising
an acquisition interface configured to acquire an image representing a road surface imaged by the camera, and
a controller configured to determine whether the road surface is wet or dry on the basis of a spatial change in luminance of pixels in a continuous region included in the image,
wherein the controller is configured to calculate a parameter corresponding to a spatial frequency of the luminance and to determine a wet region of the road surface on the basis of the calculated parameter, and wherein the controller is configured to extract a frequency continuous portion in which the parameter corresponding to the spatial frequency of the continuous region of the image is continuous across at least a predetermined length, and when a plurality of frequency continuous portions is extracted, to determine that the road surface is wet at the frequency continuous portion, among the extracted plurality of frequency continuous portions, in which the parameter corresponds to a lower spatial frequency.

8. An imaging system comprising:

a temperature detector configured to measure a temperature of a road surface; and an imaging apparatus comprising a camera and a road surface state determination apparatus, the road surface state determination apparatus comprising an acquisition interface configured to acquire an image representing a road surface imaged by the camera and a signal related to the temperature of the road surface and a controller configured to determine whether the road surface is wet or dry on the basis of a luminance of pixels included in the image and to determine whether the road surface is frozen on the basis of the signal related to the temperature of the road surface, wherein the controller is configured to calculate a parameter corresponding to a spatial frequency of the luminance and to determine a wet region of the road surface on the basis of the calculated parameter, and wherein the controller is configured to extract a frequency continuous portion in which the parameter corresponding to the spatial frequency of the continuous region of the image is continuous across at least a predetermined length, and when a plurality of frequency continuous portions is extracted, to determine that the road surface is wet at the frequency continuous portion, among the extracted plurality of frequency continuous portions, in which the parameter corresponds to a lower spatial frequency.

9. A road surface state determination method comprising:

acquiring, using an acquisition interface, an image representing a road surface imaged by a camera, and determining, using a controller, whether the road surface is wet or dry on the basis of a spatial change in luminance of pixels in a continuous region included in the image, by at least calculating a parameter corresponding to a spatial frequency of the luminance and determining a wet region of the road surface on the basis of the calculated parameter, and extracting a frequency continuous portion in which the parameter corresponding to the spatial frequency of the continuous region of the image is continuous across at least a predetermined length, and when a plurality of frequency continuous portions is extracted, determining that the road surface is wet at the frequency continuous portion, among the extracted plurality of frequency continuous portions, in which the parameter corresponds to a lower spatial frequency.

* * * * *